United States Patent [19]
Bogden et al.

[11] Patent Number: 6,087,337
[45] Date of Patent: Jul. 11, 2000

[54] METHOD FOR TREATING BENIGN AND MALIGNANT PROLIFERATIVE SKIN DISEASE

[75] Inventors: Arthur E. Bogden, Hopedale; Jacques-Pierre Moreau, Upton, both of Mass.

[73] Assignee: Biomeasure Inc., Milford, Mass.

[21] Appl. No.: 08/089,410

[22] Filed: Jul. 9, 1993

Related U.S. Application Data

[63] Continuation of application No. 07/652,863, Feb. 8, 1991, abandoned.

[51] Int. Cl.$^7$ ................................................ A61K 38/16
[52] U.S. Cl. ............................ 514/16; 514/15; 514/14; 514/13; 514/12; 514/17; 514/9; 514/806
[58] Field of Search ................................ 514/12, 13, 14, 514/15, 16, 17, 9, 806; 530/311

[56] References Cited

U.S. PATENT DOCUMENTS

| | | | |
|---|---|---|---|
| 4,235,886 | 11/1980 | Freidinger et al. | 424/177 |
| 4,310,518 | 1/1982 | Freidinger et al. | 424/177 |
| 4,360,516 | 11/1982 | Freidinger et al. | 424/177 |
| 4,395,403 | 7/1983 | Bauer et al. | 424/177 |
| 4,585,755 | 4/1986 | Morgan et al. | 530/311 |
| 4,650,787 | 3/1987 | Schally et al. | 514/11 |
| 4,853,371 | 8/1989 | Coy et al. | 514/12 |
| 4,871,717 | 10/1989 | Coy et al. | 514/11 |
| 4,904,642 | 2/1990 | Coy et al. | 514/11 |

FOREIGN PATENT DOCUMENTS

| | | |
|---|---|---|
| 0175644 | 3/1986 | European Pat. Off. |
| 0187622 | 7/1986 | European Pat. Off. |
| 0 200 188 | 11/1986 | European Pat. Off. |
| 0363589 | 4/1990 | European Pat. Off. |
| 2225579 | 6/1990 | United Kingdom . |
| 2 241 167 | 8/1991 | United Kingdom . |
| 9109056 | 6/1991 | WIPO ................................... 530/311 |

OTHER PUBLICATIONS

The Merck Manual of Diagnosis and Therapy, 11$^{th}$ Ed., pp. 1451–1453, (1966).
Souqruet, Cancer, vol. 59(9), pp. 1654–1660 (May 1, 1987).
Altman et al., *Archives of Dermatology*, 125:2–3, Mar. 1989.
Cai, R. –Z., et al., Proc. Natl. Acad. Sci., 83:1896–1900 (1986).
Camisa, C., et al., Cleveland Clinic Journal of Medicine, 57(1):71–76 (1990).
Choi, Hoo–Kyun, et al., Pharmaceutical Research, 7(11):1099–1106 (1990).
Karashima, T., et al., Life Sciences, 41:1011–1019 (1987).
Neely, E.K., et al., J. Inv. Dermatol., 96(1):104–110 (Jan. 1991).
Redding, T.W. et al., Proc. Natl. Acad. Sci., 80:1078–82 (1983).
Reubi, J.C. et al., Arch. Dermatol. Res. 282:139–141 (1990).
Schally, A.V., et al., Proc. Natl. Acad. Sci. USA, 84:7275–729 (1987).
Setyono–Han, B. et al., Cancer Research, 47:1566–1569 (1987).
Siegel, R.A., et al., Cancer Research, 48:4651–4655 (1988).
Veber, Daniel F., et al., Life Sciences, 34:1371–1378 (1984).

*Primary Examiner*—Keith D. MacMillan
*Assistant Examiner*—T. D. Wessendorf
*Attorney, Agent, or Firm*—Fish and Richardson; Brian R. Morrill, Esq

[57] ABSTRACT

A method of treating a mammal suffering from benign or malignant proliferative skin disease, e.g., melanoma or malignant skin metastases of melanoma, by topically administering to the mammal at the site of said diseased skin an effective amount of a somatostatin analog containing six or more amino acids.

9 Claims, 3 Drawing Sheets

T D4   AN. #8 TREATED- DAY 4

T D7   AN. #8 TREATED- DAY 7

T D11   AN. #8 TREATED- DAY11

METHOD FOR TREATING BENIGN AND MALIGNANT PROLIFERATIVE SKIN DISEASE

This is a continuation of application Ser. No. 07/652,863, filed Feb. 8, 1991, now abandoned.

BACKGROUND OF THE INVENTION

This invention relates to the therapeutic use of somatostatin and somatostatin analog peptides.

Somatostatin is a naturally occurring tetra-decapeptide having the following amino acid sequence:

H-Ala$^1$-Gly$^2$-Cys$^3$-Lys$^4$-Asn$^5$-Phe$^6$-Phe$^7$-Trp$^8$-Lys$^9$-Thr$^{10}$-Phe$^{11}$-Thr$^{12}$-Ser$^{13}$-Cys$^{14}$-OH.

A number of somatostatin analogs have been described in the literature and patents, including analogs containing fewer than the naturally occurring fourteen amino acids. For example, Coy et al., U.S. Pat. No. 4,853,371, hereby incorporated by reference, describes octapeptides having a C-terminal NH$_2$ and D-Trp at position 4:

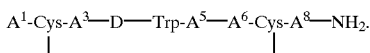

A preferred compound has D-β-napthylalanine (D-β-Nal) at positions 1 and/or 3; Tyr at position 3; and Val at position 6. (Herein, when no designation of configuration is given, the L-isomer is intended.)

SUMMARY OF THE INVENTION

Applicants have discovered that benign and malignant proliferative skin diseases, e.g., melanomas and malignant skin metastases of melanoma, express somatostatin receptors and have developed a method of treating a mammal (e.g., a human) suffering from such proliferative skin diseases, by topically administering an effective amount of a somatostatin analog containing six or more amino acids, e.g, in a pharmaceutically acceptable inert carrier, to the affected skin surface. The analog may be present in the carrier in a concentration of, e.g., at least 10 mg/ml. The analog may be applied repeatedly to the diseased skin to achieve an approximate dosage of 125 μg/cm$^2$ of skin/day.

The somatostatin analogs preferably have a four or greater amino acid sequence having at least 20% homology with the core region of somatostatin. The core region is made up of the amino acids at positions 7, 8, 9, and 10 of the naturally occurring somatostatin sequence shown above. More preferably, the somatostatin analogs have a six or seven amino acid sequence having at least 20%, even more preferably at least 50%, homology with the core region of somatostatin. As used herein, the term "somatostatin analog" includes naturally occurring somatostatin with 14 amino acids as shown in the Background of the Invention, above.

One class of somatostatin analogs that is suitable in the proliferative skin disease therapy method of the invention includes octapeptides of the formula:

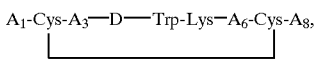
(I)

wherein A$_1$ is D-Phe, N-Ac-D-hArg(Et)$_2$-Gly, D-β-Nal, or

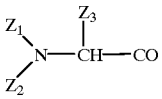

wherein each Z$_1$ and Z$_2$, independently, is H, C$_{1-12}$ alkyl, C$_{7-10}$ phenylalkyl, R$_1$CO (where R$_1$ is C$_{1-20}$ alkyl, C$_{3-20}$ alkenyl, C$_{3-20}$ alkinyl, phenyl, naphthyl, or C$_{7-10}$ phenylalkyl), or R$_2$OCO (where R$_2$ is C$_{1-10}$ alkyl or C$_{7-10}$ phenylalkyl), provided that when one of Z$_1$ or Z$_2$ is R$_1$CO or R$_2$OCO, the other must be H;

Z$_3$ is CH$_2$-Z$_4$ (where Z$_4$ is pentafluorophenyl, naphthyl, pyridyl, phenyl, or o-, m-, or, more preferably, p-substituted phenyl, where the substituent is a halogen, NH$_2$, NO$_2$, OH, or C$_{1-3}$ alkyl);

A$_3$ is Phe, o-, m-, or, more preferably, p-substituted X-Phe (where X is a halogen, H, NH$_2$, NO$_2$, OH, or C$_{1-3}$ alkyl), pentafluoro-Phe, β-Nal, Tyr, or Thr;

A$_6$ is Thr, Ser, Phe, Val, α-aminobutyric acid, or Ile, provided that when Z$_3$ is phenyl, Z$_1$ is H, and Z$_2$ is H, A$_6$ cannot be Val; and A$_8$ is Thr-NH$_2$, Trp-NH$_2$, L-β-Nal-NH$_2$, or Thr(ol) (where Thr(ol) is NHCH(CH$_2$OH)CHOHCH$_3$); or a pharmaceutically acceptable salt thereof.

The term "pharmaceutically acceptable salt" refers to a salt that retains the desired biological activity of the parent compound and does not impart any undesired toxicological effects, e.g., an acid or base addition salt. The term "hArg" refers to homoarginyl.

In formula I given above, the configuration of the molecule at the carbon atom to which Z$_3$ is bonded is not given, to indicate that the amino acid residue of which Z$_3$ is a substituent can have the D- or L- configuration.

As shown in formula I, the octapeptide somatostatin analogs useful in the present invention preferably have D-Trp at position 4.

Preferred compounds of formula I above include D-β-Nal-Cys-Tyr-D-Trp-Lys-Val-Cys-Thr-NH$_2$; D-Phe-Cys-Tyr-D-Trp-Lys-Val-Cys-β-Nal-NH$_2$; D-Phe-Cys-Tyr-D-Trp-Lys-α-Aminobutyric acid-Cys-Thr-NH$_2$; pentafluoro-D-Phe-Cys-Tyr-D-Trp-Lys-Val-Cys-Thr-NH$_2$; N-Ac-D-β-Nal-Cys-Tyr-D-Trp-Lys-Val-Cys-Thr-NH$_2$; D-β-Nal-Cys-pentafluoro-Phe-D-Trp-Lys-Val-Cys-Thr-NH$_2$; D-β-Nal-Cys-Tyr-D-Trp-Lys-Val-Cys-β-Nal-NH$_2$; D-Phe-Cys-β-Nal-D-Trp-Lys-Val-Cys-Thr-NH$_2$; D-β-Nal-Cys-Tyr-D-Trp-Lys-α-aminobutyric acid-Cys-Thr-NH$_2$; D-p-Cl-Phe-Cys-Tyr-D-Trp-Lys-α-aminobutyric acid-Cys-Thr-NH$_2$; and acetyl-D-p-Cl-Phe-Cys-Tyr-D-Trp-Lys-α-aminobutyric acid-Cys-Thr-NH$_2$. The compounds which have an aromatic, lipophilic N-terminus have the further advantage of long-lasting in vivo activity.

Other preferred octapeptide somatostatin analogs within formula I suitable for use in the present invention are:

D-Phe-Cys-Phe-D-Trp-Lys-Thr-Cys-Thr(ol) (SMS 201-995);

D-Phe-Cys-Tyr-D-Trp-Lys-Val-Cys-Trp-NH$_2$ (RC-160);

and

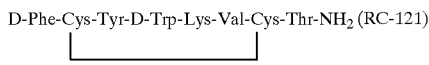

Other somatostatin analogs suitable for the present invention are hexapeptides such as: cyclo(Pro-Phe-D-Trp-Lys-Thr-Phe) which has been shown to have the biological properties of somatostatin; and cyclo(N-Me-Ala-Tyr-D-Trp-Lys-Val-Phe), which is 50–100 times more potent than naturally occurring somatostatin for the inhibition of insulin, glucagon, and growth hormone release.

The present invention also covers the use of heptapeptide analogs of the formula:

$$A_1\text{-}A_2\text{-}A_3\text{-}A_4\text{-}A_5\text{-}Cys\text{-}A_7\text{-}A_8, \quad (II)$$

wherein $A_1$ is

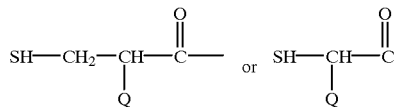

(where Q is H or a $C_1$–$C_8$ alkyl group);

$A_2$ is o-, m-, or p-substituted X-Phe or X-D-Phe (where X is H, halogen, $NH_2$, $NO_2$, OH, $C_1$–$C_3$ alkyl, or $C_1$–$C_3$ alkoxy);

$A_3$ is X-Trp, X-D-Trp, α-N-methyl-X-Trp, or α-N-methyl-D-X-Trp (where X is a substituent on the benzene ring and is H, halogen, $NH_2$, $NO_2$, OH, $C_1$–$C_3$ alkyl, or $C_1$–$C_3$ alkoxy);

$A_4$ is Lys, α-N-methyl-Lys, or ε-N-$R_1$-Lys (where $R_1$ is $C_1$–$C_3$ alkyl);

$A_5$ is Val or Thr;

$A_7$ is Pro or

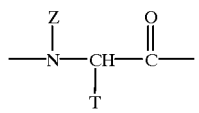

where Z is H or $CH_3$ and T is H, $CH_2OH$, $CH_2CH_2OH$, $CH_2CH_2CH_2OH$, $CH(CH_3)OH$, isobutyl, benzyl (substituted in the o-, m-, or p-positions with H, halogen, $NH_2$, $NO_2$, OH, $C_1$–$C_3$ alkyl, or $C_1$–$C_3$ alkoxy), $CH_2$-β-naphthyl (substituted on the benzene ring with H, halogen, $NH_2$, $NO_2$, OH, $C_1$–$C_3$ alkyl, or $C_1$–$C_3$ alkoxy), or $CH_2$-pyridyl (substituted on the benzene ring with H, halogen, $NH_2$, OH, $C_1$–$C_3$ alkyl, or $C_1$–$C_3$ alkoxy; and $A_8$ is

(where $R_2$ is H or $C_1$–$C_3$ alkyl), $CH_2OH$, $CH_2OCR_3$ (where $R_3$ is $C_1$–$C_3$ alkyl, $C_8$–$C_{12}$ aralkyl, or phenoxy), or

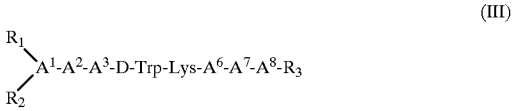

(where $R_4$ is H or $C_1$–$C_3$ alkyl and $R_5$ is H, $C_1$–$C_3$ alkyl, phenyl, or $C_7$–$C_{10}$ aralkyl); or a pharmaceutically acceptable salt thereof.

Further octapeptide formulas suitable for the present invention are linear somatostatin analogs:

$$\begin{array}{c} R_1 \\ \diagdown \\ \diagup \\ R_2 \end{array} A^1\text{-}A^2\text{-}A^3\text{-}D\text{-}Trp\text{-}Lys\text{-}A^6\text{-}A^7\text{-}A^8\text{-}R_3 \quad (III)$$

wherein $A^1$ is a D-isomer of any of Ala, pyridyl-Ala, Leu, Ile, Val, Met, Nle, Trp, β-Nal, o-X-Phe (wherein X is H, $CH_3$, Cl, Br, F, OH, $OCH_3$, or $NO_2$), p-X-Phe (wherein X is H, $CH_3$, Cl, Br, F, OH, $OCH_3$, or $NO_2$), 2,4-dichloro-Phe, or pentafluoro-Phe;

$A^2$ is any of Ala, pyridyl-Ala, Leu, Ile, Val, Met, Nle, Trp, β-Nal, o-X-Phe (wherein X is H, $CH_3$, Cl, Br, F, OH, $OCH_3$, or $NO_2$), 2,4-dichloro-Phe, or pentafluoro-Phe;

$A^3$ is any of Ala, pyridyl-Ala, Leu, Ile, Val, Met, Nle, Trp, Tyr, β-Nal, o-X-Phe (wherein X is H, $CH_3$, Cl, Br, F, OH, $OCH_3$, or $NO_2$), p-X-Phe (wherein X=H, $CH_3$, Cl, Br, F, OH, $OCH_3$, or $NO_2$), 2,4-dichloro-Phe, or pentafluoro-Phe;

$A^6$ is any of Ala, pyridyl-Ala, Leu, Ile, Val, Lys, Met, Nle, Thr-$R_4$, Trp, Ser-$R_4$, β-Nal, o-X-Phe (wherein X is $CH_3$, Cl, Br, F, OH, $OCH_3$, or $NO_2$), p-X-Phe (wherein X is $CH_3$, Cl, Br, F, OH, $OCH_3$, or $NO_2$), 2,4-dichloro-Phe, or pentafluoro-Phe;

$A^7$ is any of Ala, pyridyl-Ala, Leu, Ile, Val, Met, Nle, Trp, β-Nal, o-X-Phe (wherein X is H, $CH_3$, Cl, Br, F, OH, $OCH_3$, or $NO_2$), p-X-Phe (wherein X is H, $CH_3$, Cl, Br, F, OH, $OCH_3$, or $NO_2$), 2,4-dichloro-Phe, or pentafluoro-Phe;

$A^8$ is a D- or L-isomer of any of Ala, pyridyl-Ala, Leu, Ile, Ser-$R_4$, Thr-$R_4$, Val, Met, Nle, Trp, β-Nal, o-X-Phe (wherein X is $CH_3$, Cl, Br, F, OH, $OCH_3$, or $NO_2$), p-X-Phe (wherein X=$CH_3$, Cl, Br, F, OH, $OCH_3$, or $NO_2$), 2,4-dichloro-Phe, or pentafluoro-Phe;

each of $R_1$ and $R_2$, independently, is any of H, lower acyl, or lower alkyl; and $R_3$ is H, $NH_2$, or lower alkyl; provided that at least one of $A^1$ and $A^8$ must be an aromatic amino acid; and further provided that if either $A^2$ or $A^7$ is an aromatic amino acid, then $A^8$ cannot be an aromatic amino acid; and further provided that $R_4$ may be nothing or may be carbohydrate, e.g., $C_x(H_2O)_y$, where x is 1–18 and y is 1–16, linked through the hydroxyl group of Ser or Thr; or a pharmaceutically acceptable salt thereof.

For use, a therapeutically effective amount of the somatostatin analog is applied to the site of diseased skin or is combined with a pharmaceutically acceptable carrier substance or excipient, e.g., a spreadable cream, gel, lotion, or ointment, to form a therapeutic compound that will achieve transport of the analog through the skin. The penetration of the somatostatin analog to the diseased tissue may be accomplished by a variety of methods known to those of ordinary skill in this field.

For example, the analog may be applied directly or mixed with a carrier substance and then mechanically rubbed into the skin in an affected area which allows the analog to penetrate the skin. The analog may also be contained in liposomes that are mechanically applied to diseased skin. Furthermore, the somatostatin analog may be incorporated into a transdermal patch that is applied to the diseased skin. Preferably, the penetration resulting from these methods may be enhanced with a chemical transdermal delivery agent such as dimethyl sulfoxide (DMSO) or the nonionic surfactant, n-decylmethyl sulfoxide (NDMS) as described in Choi et al., Pharmaceutical Res., 7 (11): 1099–1106 (1990). Furthermore, the penetration of the somatostatin analog through the skin may be accomplished by iontophoresis by mixing the analog with a carrier substance containing negative or positive ions and incorporating the resulting therapeutic comupound into a transdermal patch. The therapeutic composition can also be in the form of a biodegradable sustained release formulation for topical administration at the site of the diseased skin.

The topical treatment method of the invention provides effective therapy for proliferative skin diseases, e.g., melanomas and malignant skin metastases of melanomas, at high dosages, yet these high dosages do not cause significant toxic side effects.

Other features and advantages of the invention will be apparent from the following description of the preferred embodiments thereof, and from the claims.

DESCRIPTION OF THE PREFERRED EMBODIMENTS

The drawings will first be briefly described.

STRUCTURE

Figure 1:
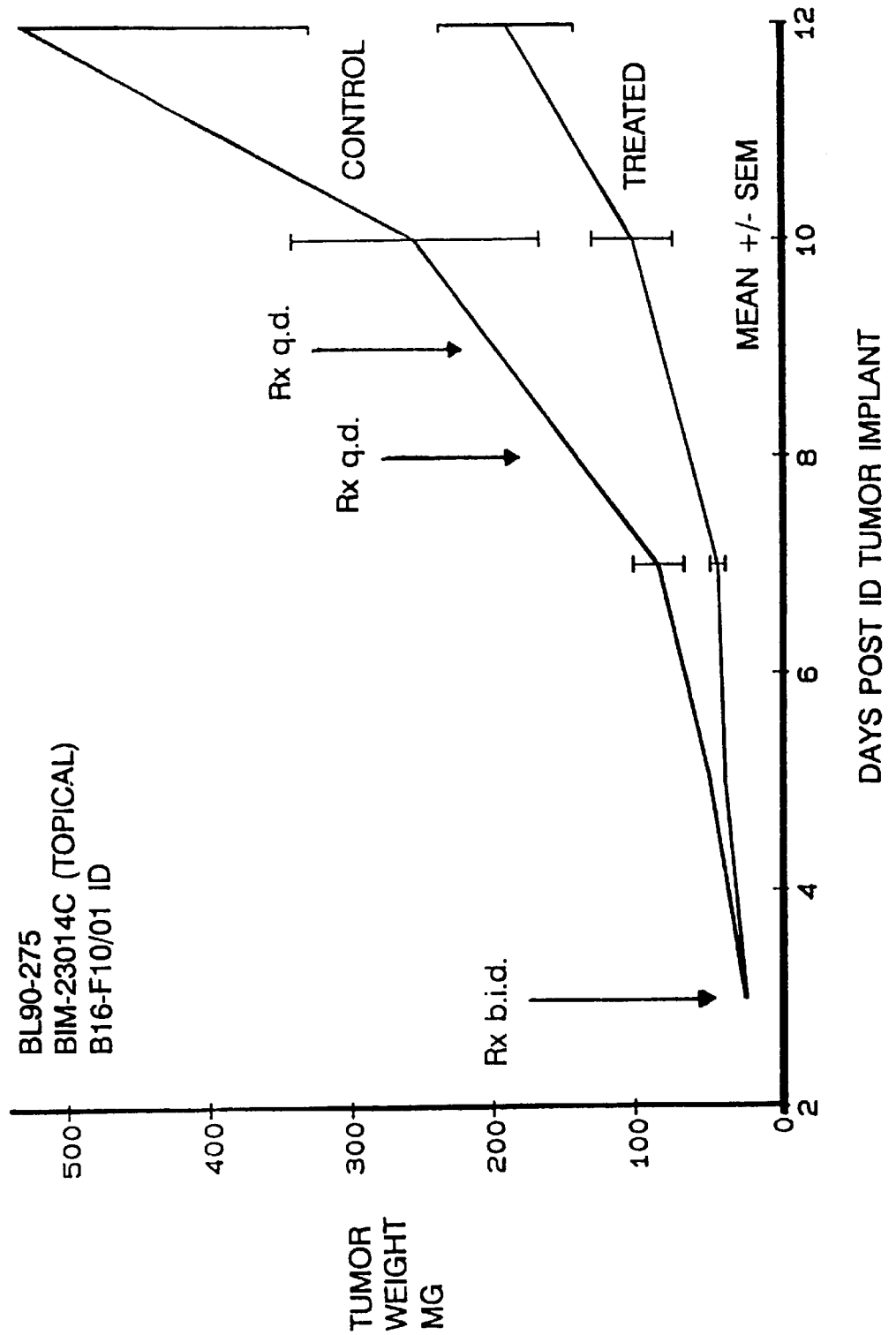
FIG. 1 is a graph illustrating the effect of a somatostatin analog (referred to in the graph as "BIM23014C") on the growth of a B16-F10 melanoma.

Suitable compounds for treatment of proliferative skin diseases are the somatostatin analogs described in the Summary of the Invention, above. Examples of preferred analogs include the following:

D-β-Nal-Cys-Tyr-D-Trp-Lys-Val-Cys-Thr-$NH_2$; D-Phe-Cys-Tyr-D-Trp-Lys-Val-Cys-Trp-$NH_2$; D-Phe-Cys-Phe-D-Trp-Lys-Thr-Cys-Thr(ol); D-p-Cl-Phe-Cys-Tyr-D-Trp-Lys-Val-Cys-Thr-$NH_2$; and D-Phe-Cys-Tyr-D-Trp-Lys-Val-Cys-β-Nal; ("Nal" refers to naphthylalanine.)

Other suitable somatostatin analogs include the naturally occurring tetra-decapeptide somatostatin and the analogs described in Coy et al., U.S. Pat. Nos. 4,904,642, 4,871,717, and 4,853,371; Freidinger et al., U.S. Pat. Nos. 4,360,516, and 4,310,518; Nestor, EPA 0,363,589; and Bauer et al., U.S. Pat. No. 4,395,403; all hereby incorporated by reference.

Synthesis

The synthesis of one octapeptide somatostatin analog follows. Other analogs can be prepared by making appropriate modifications, within the ability of one of ordinary skill in this field, of the following synthetic method.

The first step in the preparation of D-β-naphthyl-alanine-Cys-Tyr-D-Trp-Lys-Val-Cys-Thr-$NH_2$ was the preparation of the intermediate tert-butyloxycarbonyl-D-β-naphthylalanine-S-methylbenzyl-Cys-Tyr-D-Trp-$N^{68}$-benzyloxy-carbonyl-Lys-Val-S-methyl-benzyl-Cys-O-benzyl-Thr-benzyhydrylaminine resin, as follows.

Benzhydrylamine-polystyrene resin (Vega Biochemicals, Inc.), in the chloride ion form, was placed in the reaction vessel of a Beckman 990B peptide synthesizer programmed to perform the following reaction cycle: (a) methylene chloride; (b) 33% trifluoroacetic acid in methylene chloride (2 times for 1 and 25 min. each); (c) methylene chloride; (d) ethanol; (e) methylene chloride; (f) 10% triethylamine in chloroform.

The neutralized resin was stirred with Boc-O-benzyl-threonine and diisopropylcarbodiimide (1.5 mmole each) in methylene chloride for 1 h and the resulting amino acid resin was then cycled through steps (a) to (f) in the above wash program. The following amino acids (1.5 mmole) were then coupled successively by the same procedure: Boc-S-methylbenzyl-Cys, Boc-Val, Boc-Ne-benzyloxy-carbonyl-lysine, Boc-D-Trp, Boc-Tyr, Boc-S-methylbenzyl-Cys, Boc-D-β-naphthylalanine.

The resin was washed and dried and then mixed with anisole (4 ml) and anhydrous hydrogen fluoride (36 ml) at 0° C. and stirred for 45 min. (one can also use thioanisole, trifluoroacetic acid, and trifluoromethane sulfonic acid at a ratio of 1:90:9, for 6h). Excess hydrogen fluoride was evaporated rapidly under a stream of dry nitrogen and free peptide precipitated and washed with ether. The crude peptide was then dissolved in 800 ml of 90% acetic acid to which was added $I_2$ in methanol until a permanent brown color was present. The solution was then stirred for 1 h before removing the solvent in vacuo. The resulting oil was dissolved in a minimum volume of 50% acetic acid and eluted on a column (2.5×100 mm) of Sephadex G-25. Fractions containing a major component by uv absorption and thin layer chromatography (tlc) were then pooled, evaporated to a small volume, and applied to a column (2.5×50 cm) of Whatman LRP-1 octadecylsilane (15–20 μM).

The column was eluted with a linear gradient of 10–50% acetonitrile in 0.1% trifluoroacetic acid in water. Fractions were examined by tlc and analytical high performance liquid chromatography (hplc) and pooled to give maximum purity and if desired, a different salt prepared, e.g., acetate or phosphate. Repeated lyophilization of the solution from water gave 170 mg of the product as a white, fluffy powder.

The product was found to be homogeneous by hplc and tlc. Amino acid analysis of an acid hydrolysate confirmed the composition of the octapeptide.

The octapeptides of the invention having the formulae pentafluoro-D-Phe-Cys-Tyr-D-Trp-Lys-Val-Cys-Thr-$NH_2$, D-Phe-Cys-Tyr-D-Trp-Lys-α-aminobutyric acid-Cys-Thr-$NH_2$, N-Ac-D-β-Nal-Cys-Tyr-D-Trp-Lys-Val-Cys-Thr-$NH_2$, D-β-Nal-Cys-pentafluoro-Phe-D-Trp-Lys-Val-Cys-Thr-$NH_2$, D-β-Nal-Cys-Tyr-D-Trp-Lys-Val-Cys-β-Nal-$NH_2$, D-Phe-Cys-Tyr-D-Trp-Lys-Val-Cys-β-Nal-$NH_2$, D-β-Nal-Cys-Tyr-D-Trp-Lys-α-aminobutyric acid-Cys-Thr-$NH_2$. D-p-Cl-Phe-Cys-Tyr-D-Trp-Lys-α-aminobutyric acid-Cys-Thr-$NH_2$, and acetyl-D-p-Cl-Phe-Cys-Tyr-D-Trp-Lys-α-aminobutyric acid-Cys-Thr-$NH_2$ were made according to methods analogous to those described above. Similar methods may be used to synthesize the hexa-, hepta-, and other octapeptides useful in the present invention. Moreover, the synthetic methods disclosed in U.S. Pat. Nos. 4,360,516, 4,310,518, and 4,395,403 are incorporated herein by reference.

Response of Intradermally Implanted B16-F10 Melanoma Xenografts to Topically Applied Somatuline BIM-23014C Implantation of Melanoma Eighteen BALB/c derived athymic nude female mice were implanted intradermally (ID), on the right flank, with a 0.02 to 0.05 ml suspension of in vitro propagated B16-F10 melanoma cells suspended in a normal saline solution. Implantation was done with a 23 gauge needle attached to a 1.0 ml syringe on day 0. Such an intradermal implant of the murine B16-F10 melanoma is essentially orthotopic and gives rise to an extremely fast growing tumor. By day 2, flat melanotic growths were evident at the injection site. The lesions resembled in situ melanomas.

Treatment

Somatuline (D-$\beta$-Nal-Cys-Tyr-D-Trp-Lys-Val-Cys-Thr-$NH_2$, available from Biomeasure, Inc. under the product code BIM-23014C) was added to a 50% DMSO in saline solution at a concentration of 10 mgs/ml. After wiping the skin with a gauze pad wet with isopropyl alcohol, a drop (approximately 0.05 ml) of the Somatuline solution was applied to the skin surface of the mice over the melanotic lesion. The solution was rubbed into the skin for approximately 1 minute with a latex gloved (Baxter Scientific Products/Flexam) finger. Well over half of the drop of Somatuline was not absorbed and was lost after the rubbing-in procedure. The controls were treated identically with 50% DMSO in saline solution without any somatostatin analog. Topical treatments were applied twice daily for 11 days beginning on day 3 post implantation.

TREATMENT RESULTS

| Group No. | Treatment | Tumor Wt. (mgs) Day 12 | % T/C |
|---|---|---|---|
| 1 | DMSO/Saline vehicle, 0.05 ml, topical, b.i.d., q.d. 3–14 | 531.6 ± 205 | — |
| 2 | BIM-23014C, 0.05 ml, topical of DMSO/Saline vehicle containing 10 mg/ml of BIM-23014, b.i.d., q.d. 3–14 | 185.9 ± 47 | 35 |

Figure 2A:
FIG. 2 is a series of photographs showing the melanoma growth progression in a mouse treated with BIM23014C on days 4, 7, and 11.
Figure 2B:
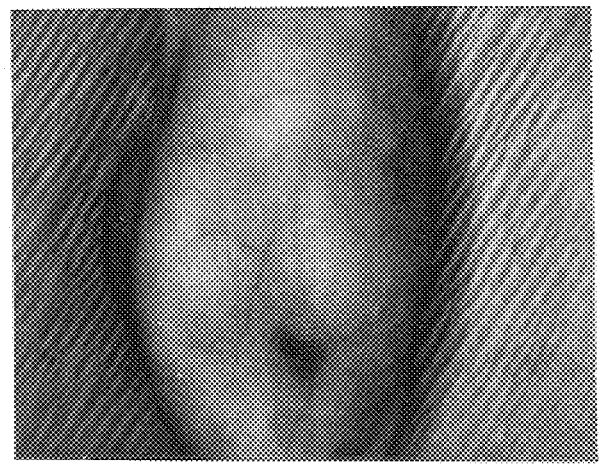
Figure 2C:
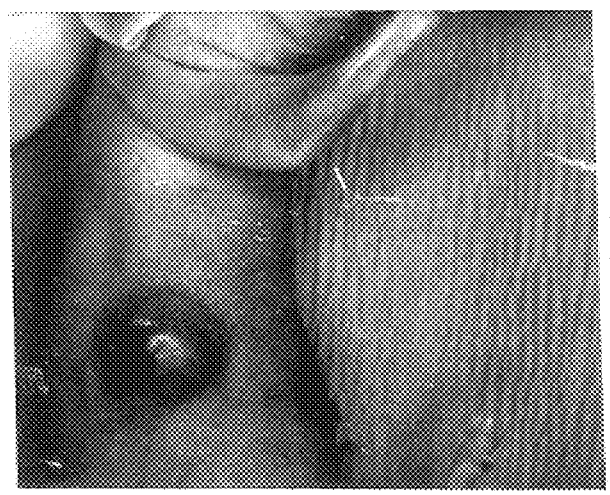
Figure 3A:
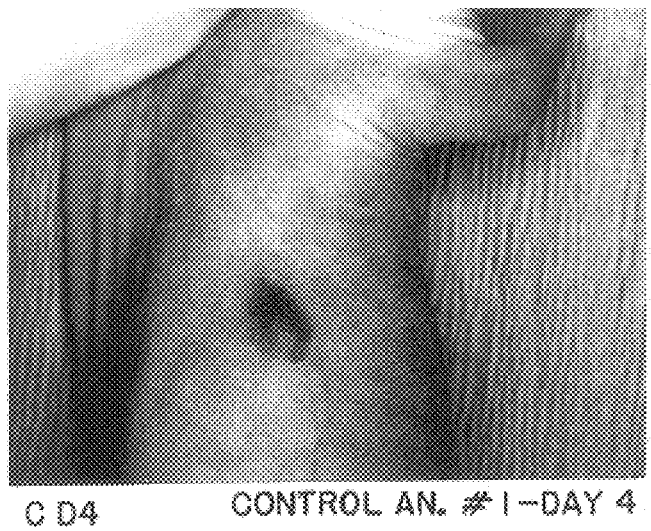
FIG. 3 is a series of photographs showing the melanoma growth progression in a control mouse on days 4, 7, and 11.
Figure 3B:
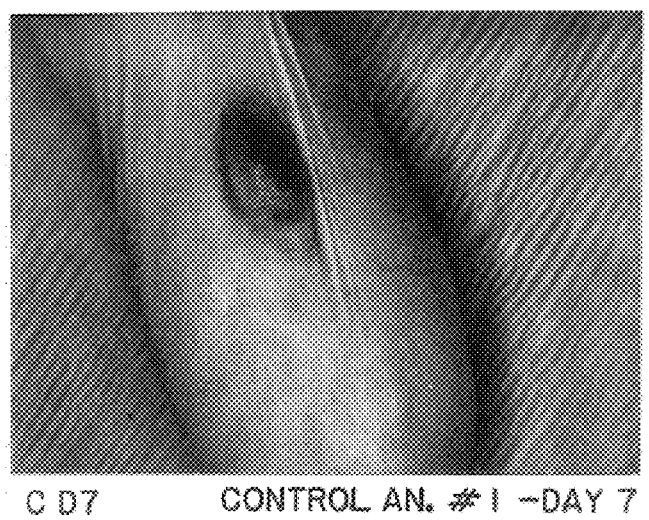
Figure 3C:
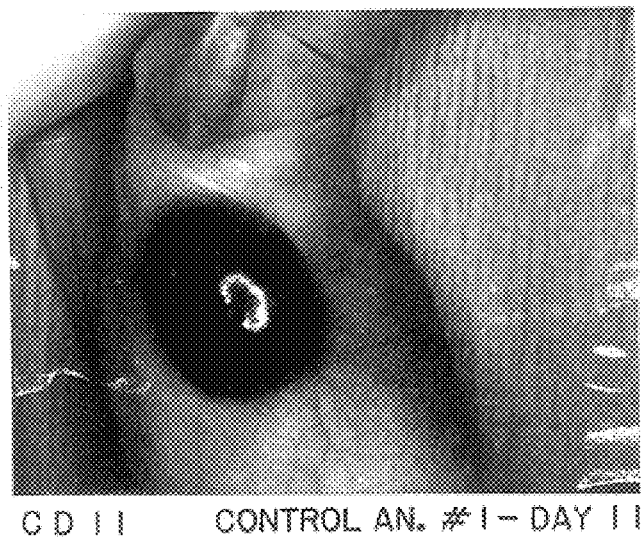

FIG. 1 shows tumor growth curves for the experiment described above. FIGS. 2 and 3 show photographs of melanotic lesions on mice taken on days 4, 7, and 11. These photos in FIG. 2 and the tumor growth curves in FIG. 1 show the clear growth inhibition of the melanotic lesion by the Somatuline solution, compared to the control curves in FIG. 1 and the untreated lesions on control mice shown in FIG. 3.

Therapy

The invention provides effective treatment for benign and malignant proliferative skin diseases by the use of the above-described analogs, and somatostatin hexapeptide or higher analogs generally, when administered as described above. The benign and malignant skin diseases described above include melanomas and malignant skin metastases of melanoma, reoccurring keratosis, non-invasive basal cellular epithelioma pagetoid, and basal cell carcinoma. The somatostatin analogs may be administered directly to the diseased skin or may be used as a follow-up treatment after surgical excision or radiotherapy of the primary tumor to prevent reoccurrence.

Keratosis includes pre-epitheliomatosis, actinic keratosis (due to overexposure to the sun), and keratosis due to ageing. The somatostatin analogs may also be administered for preventative treatment, e.g., for actinic and ageing keratosis.

Other embodiments are within the following claims.

What is claimed is:

1. A method of treating a mammal suffering from benign or malignant skin melanomas or metastases of malignant melanomas, comprising topically administering to said mammal at the site of said melanoma an effective amount of a cyclic octapeptide somatostatin analog of the formula:

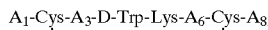

wherein $A_1$ is D-Phe, N-Ac-D-hArg(Et)$_2$-Gly, D-$\beta$-Nal, or

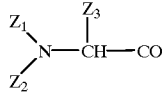

wherein the C bonded to $Z_3$ has a D-configuration, wherein each $Z_1$ and $Z_2$, independently, is H, $C_{1-12}$ alkyl, $C_{7-10}$ phenylalkyl, $R_1CO$, where $R_1$ is $C_{1-20}$ alkyl, $C_{3-20}$ alkenyl, $C_{3-20}$ alkinyl, phenyl, naphthyl, or $C_{7-10}$ phenylalkyl, or $R_2OCO$, where $R_2$ is $C_{1-10}$ alkyl or $C_{7-10}$ phenylalkyl, wherein when one of $Z_1$ or $Z_2$ is $R_1CO$ or $R_2OCO$, the other is H;

$Z_3$ is $CH_2$-$Z_4$, wherein $Z_4$ is pentafluorophenyl, naphthyl, pyridyl, phenyl, or o-, m-, or p-substituted phenyl, where the substituent is a halogen, $NH_2$, $NO_2$, OH, or $C_{1-3}$ alkyl;

$A_3$ is Phe, o-, m-, or p-substituted X-Phe, where X is a halogen, H, $NH_2$, $NO_2$, OH, or $C_{1-3}$ alkyl, pentafluoro-Phe, $\beta$-Nal, or Tyr;

$A_6$ is Thr, Ser, Val, or $\alpha$-aminobutyric acid; and $A_8$ is Thr-$NH_2$, Trp-$NH_2$, L-$\beta$-Nal-$NH_2$, or Thr(ol); or a pharmaceutically acceptable salt thereof.

2. The method of claim 1, wherein said somatostatin analog is

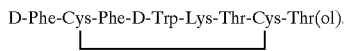

3. The method of claim 1, wherein said somatostatin analog is

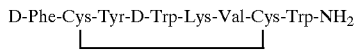

4. The method of claim 1, wherein said somatostatin analog is

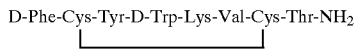

5. The method of claim 1, wherein said octapeptide is

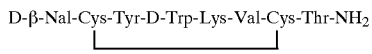

or a pharmaceutically acceptable salt thereof.

6. The method of claim 1, wherein said octapeptide is

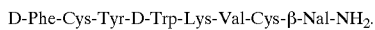
D-Phe-Cys-Tyr-D-Trp-Lys-Val-Cys-β-Nal-NH₂.

7. A method of treating a mammal suffering from benign or malignant skin melanomas or metastases of malignant melanomas, comprising topically administering to said mammal at the site of said melanoma an effective amount of a cyclic hexapeptide somatostatin analog of the formula cyclo(N-Me-Ala-Tyr-D-Trp-Lys-Val-Phe) or cyclo(Pro-Phe-D-Trp-Lys-Thr-Phe).

8. A method of treating a mammal suffering from benign or malignant skin melanomas or metastases of malignant melanomas, comprising topically administering to said mammal at the site of said melanoma an effective amount of naturally occurring somatostatin.

9. A method of treating a mammal suffering from benign or malignant skin melanomas or metastases of malignant melanomas, comprising topically administering to said mammal at the site of said melanoma an effective amount of a linear octapeptide somatostatin analog of the formula

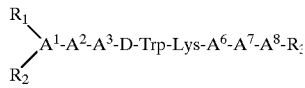
$$\begin{matrix} R_1 \\ \phantom{xx} \diagdown \\ \phantom{xxx} A^1\text{-}A^2\text{-}A^3\text{-}D\text{-}Trp\text{-}Lys\text{-}A^6\text{-}A^7\text{-}A^8\text{-}R_3 \\ \phantom{xx} \diagup \\ R_2 \end{matrix}$$

wherein $A^1$ is a D-isomer of Ala, pyridyl-Ala, Leu, Ile, Val, Met, Nle, Trp, β-Nal, o-X-Phe, wherein X is H, CH₃, Cl, Br, F, OH, OCH₃, or NO₂, p-X-Phe, wherein X is H, CH₃, Cl, Br, F, OH, OCH₃, or NO₂, 2,4-dichloro-Phe, or pentafluoro-Phe;

$A^2$ is Ala, pyridyl-Ala, Leu, Ile, Val, Met, Nle, Trp, β-Nal, o-X-Phe, wherein X is H, CH₃, Cl, Br, F, OH, OCH₃, or NO₂, 2,4-dichloro-Phe, or pentafluoro-Phe;

$A^3$ is Ala, pyridyl-Ala, Leu, Ile, Val, Met, Nle, Trp, Tyr, β-Nal, o-X-Phe, wherein X is H, CH₃, Cl, Br, F, OH, OCH₃, or NO₂, p-X-Phe, wherein X is H, CH₃, Cl, Br, F, OH, OCH₃, or NO₂, 2,4-dichloro-Phe, or pentafluoro-Phe;

$A^6$ is Ala, pyridyl-Ala, Leu, Ile, Val, Lys, Met, Nle, Thr-R₄, Trp, Ser-R₄, β-Nal, o-X-Phe, wherein X is CH₃, Cl, Br, F, OH, OCH₃, or NO₂, p-X-Phe, wherein X is CH₃, Cl, Br, F, OH, OCH₃, or NO₂, 2,4-dichloro-Phe, or pentafluoro-Phe;

$A^7$ is Ala, pyridyl-Ala, Leu, Ile, Val, Met, Nle, Trp, β-Nal, o-X-Phe, wherein X is H, CH₃, Cl, Br, F, OH, OCH₃, or NO₂, p-X-Phe, wherein X is H, CH₃, Cl, Br, F, OH, OCH₃, or NO₂, 2,4-dichloro-Phe, or pentafluoro-Phe;

$A^8$ is a D- or L-isomer of Ala, pyridyl-Ala, Leu, Ile, Ser-R₄, Thr-R₄, Val, Met, Nle, Trp, β-Nal, o-X-Phe, wherein X is CH₃, Cl, Br, F, OH, OCH₃, or NO₂, p-X-Phe, wherein X is CH₃, Cl, Br, F, OH, OCH₃, or NO₂, 2,4-dichloro-Phe, or pentafluoro-Phe;

each of $R_1$ and $R_2$, independently, is H, lower acyl, or lower alkyl; and $R_3$ is H, NH₂, or lower alkyl; wherein at least one of $A^1$ and $A^8$ is an aromatic amino acid; and wherein when either $A^2$ or $A^7$ is an aromatic amino acid, then $A^8$ cannot be an aromatic amino acid; and wherein $R_4$ is nothing or $C_x(H_2O)_y$, where x is 1–18 and y is 1–16, linked through the hydroxyl group of Ser or Thr; or a pharmaceutically acceptable salt thereof.

* * * * *